United States Patent [19]

Chiulli

[11] 4,038,985
[45] Aug. 2, 1977

[54] DEVICE FOR REPAIRING ARTERIES

[75] Inventor: Robert D. Chiulli, Somerville, Mass.

[73] Assignee: Medico Developments, Inc., Somerville, Mass.

[21] Appl. No.: 620,393

[22] Filed: Oct. 7, 1975

[51] Int. Cl.² ........................................... A61B 17/22
[52] U.S. Cl. ................................................. 128/304
[58] Field of Search ................... 128/303 R, 304, 305, 128/311, 334 R, 328, 341, 348

[56] References Cited

U.S. PATENT DOCUMENTS

| | | | |
|---|---|---|---|
| 866,180 | 9/1907 | Ball | 128/341 X |
| 1,268,576 | 6/1918 | Jensen | 128/341 |
| 1,737,488 | 11/1929 | Zohlen | 128/341 |
| 3,176,690 | 4/1965 | H'Doubler | 128/348 |
| 3,230,949 | 1/1966 | Rodriguez-Olleros | 128/305 X |
| 3,435,826 | 4/1969 | Fogarty | 128/348 |
| 3,931,820 | 1/1976 | Bucalo | 128/304 |

OTHER PUBLICATIONS

Willman et al., "Carotid Occlusive Diseases," IN Davis-Christopher, Textbook of Surgery, Chap. VI, Sec. 2, 1683–1692, 1972.

Fogarty, "Acute Arterial Occlusion," IN Davis-Christopher, Textbook of Surgery, Chap. VI, Sec. 8, 1701–1708, 1972.

*Primary Examiner*—Channing L. Pace
*Attorney, Agent, or Firm*—Scott R. Foster

[57] ABSTRACT

The device comprises a substantially rigid member having a rounded first end and a body portion generally circular in cross section and conical in longitudinal section extending therefrom to a second end. The substantially rigid member has on the body portion thereof edge means extending generally longitudinally thereof and adapted to engage the interior walls of an artery, or the like. Upon insertion of the device in an opened artery, the device insures the centering of a catheter attached thereto within the artery, supports the artery walls, upon turning of the device operates by way of the edge means to ream the artery interior, and deflects and guides a penetrating needle point during the patching operation.

9 Claims, 11 Drawing Figures

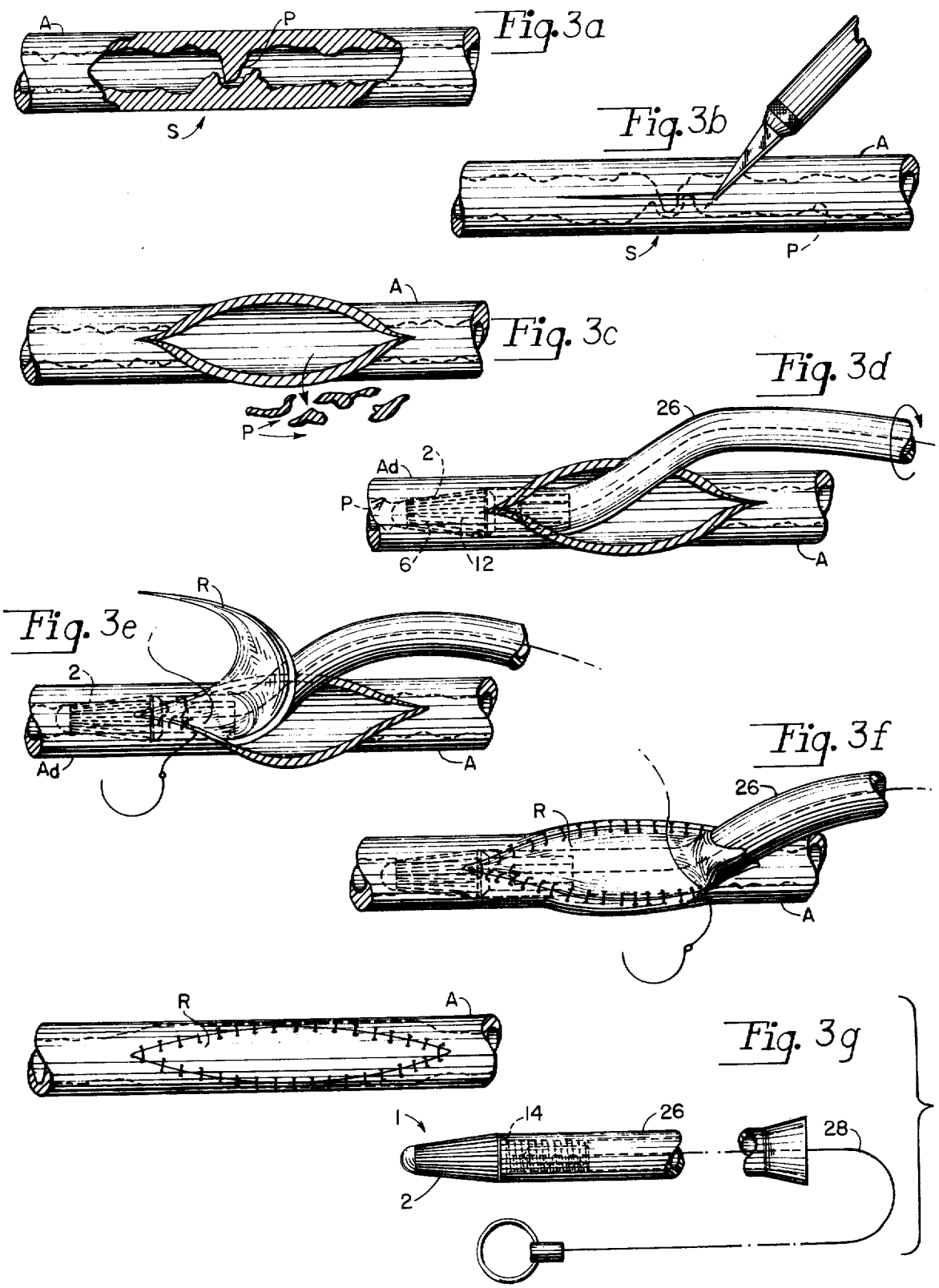

DEVICE FOR REPAIRING ARTERIES

BACKGROUND OF THE INVENTION

1. Field of the Invention

The invention relates to surgical devices and procedures and is directed more particularly to a device for repairing arteries.

2. Description of the Prior Art

FIG. 3a depicts a representation of an artery A occluded by atherosclerotic plaque P. In performing an endarterectomy, the artery is incised (FIG. 3b) over the occluded site S and the plaque P removed (FIG. 3c). After the plaque has been removed, it is necessary to taper the edges of the plaque P remaining in the unincised distal portion of the artery A$d$, to minimize the possibility of thrombus formation and/or peripheral embolization. After tapering the plaque P, a venous catheter is selected having an outside diameter comparable to the desired lumen diameter of the artery A. The catheter is pointed by making a diagonal cut across its diameter (not shown). The catheter is then guided, point-first, into the incision and its point piloted in the distal intact artery A$d$ (not shown). The catheter thereby acts to support the artery, thus maintaining the lumen diameter while a venous patch is sewn over incision. The patch is sewn into place over the catheter until only enough of the incision remains unclosed to permit escape of the catheter. The catheter is then withdrawn and the patch closed, thereby completing the endarterectomy.

The above procedure presents certain problems.

Tapering the distal plaque must be done in order to provide a gradual change in vessel lumen diameter and to eliminate any ridge or shelf for thrombus formation. Presently, distal plaque is extracted by use of forceps, frequently leaving a rough edge and oftentimes affecting a less than complete extraction of plaque.

Proper centering of the catheter in the artery or vessel is helpful in that the catheter acts as a form which supports the incised portions of the artery and a patch to be sewn thereto, facilitating alignment of the incised portions and the patch. Under present procedures, the catheter is cut on an angle, creating an eccentric point, and inserted into the distal portion of the artery. Inasmuch as the point is eccentric, being on the periphery of the catheter, it encounters irregularities on the inside wall of the artery, such as deposits of plaque and is displaced inwardly of the arterial wall, carrying the catheter to an eccentric position.

In patching the incision, the soft catheter at the site of the patch often is penetrated by the needle, interfering with a clean accurate suturing operation.

SUMMARY OF THE INVENTION

It is, therefore, an object of the invention to provide a device for surgical use in repairing incised arteries and the like which will center an attached catheter in the opened artery to provide a concentric support and which will serve as a guide and deflector to facilitate sewing of the incised portions of the artery to each other or to a patch or by-pass member.

It is a further object to provide a device which in endarterectomy procedures can be used to taper the atherosclerotic plaque of the distal artery.

A still further object is to provide such a device which may be used in conjunction with presently available catheters.

Another object is to provide such a device which is economical to manufacture and use, and which requires no maintenance or care prior to or after use.

With the above and other objects in view, as will hereinafter appear, a feature of the present invention is the provision of a device for surgical use in repairing arteries and the like, the device comprising a substantially rigid member having a rounded first end and a body portion generally circular in cross section and conical in longitudinal section extending therefrom to a second end, the substantially rigid member having generally longitudinally disposed edge means on the body portion, the edge means being adapted to engage interior walls of an artery. The device, upon insertion in an artery, operates to center an attached catheter therein, operates to support the artery walls and patch in the area of the incision upon turning of the device operates by way of the edge means to ream the interior wall of the artery, whereby to form a taper in the distal plaque, and operates to deflect an incoming surgical needle point during the suturing stage.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention from which its novel features and advantages will be apparent.

FIGS. 3a–3g illustrate a method of artery repair utilizing the device of FIG. 1 and FIGS. 2a–2c.

DESCRIPTION OF THE PREFERRED EMBODIMENTS

Figure 1:
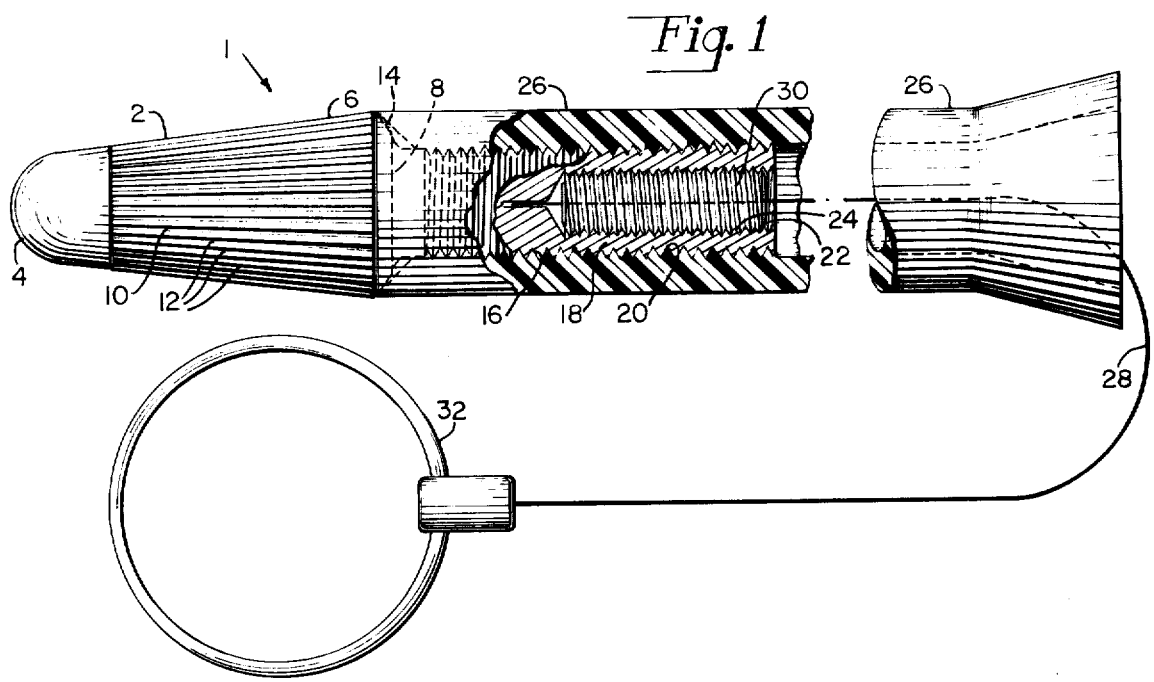
FIG. 1 is a side elevational view of one form of device illustrative of an embodiment of the invention, the device being shown connected to a standard catheter and a safety wire.

Referring to FIG. 1, it will be seen that a preferred embodiment of the present invention comprises a device 1, including a substantially rigid member 2 having a rounded first end 4 and an outwardly flairing or conical body portion 6 extending to a second end 8. The body portion 6 is generally circular in cross section and is provided with a generally longitudinally disposed edge means 10 which may be in the form of a series of knurls or ridges 12. A chamfered wall portion 14 may be provided, extending between the knurls 12 and the second end 8 of the member 2.

Extending from the second end 8, there is a connecting means 16 for connecting the member 2 to a catheter and also to a safety wire. To affect connection to the catheter, the connecting means, which may be in the form of an elongated shank 18, is provided with a first means in the form of external screw threads 20 which are adapted to engage the interior wall of the catheter composed of flexible plastic tubing. To effect connection to the safety wire, the shank 18 is provided with a second means in the form of a bore 22 having internal screw threads 24 which receive a threaded male member secured to one end of the safety wire.

The device may be provided with flow channels (not shown), to facilitate the passage of fluids from the catheter into the artery.

Still referring to FIG. 1, it will be seen that a catheter 26 receives the threaded shaft 18, the threads 20 securely engaging the inner wall of the catheter. A safety wire 28 having a threaded male member 30 at one end is attached to the member 6 by threaded engagement of the member 30 and the internal threads 24 of the shaft 18. The safety wire 28 is preferably provided with a pull ring 32 to facilitate extraction of the member 2 under certain circumstances, as will be further discussed below.

Figure 2A:
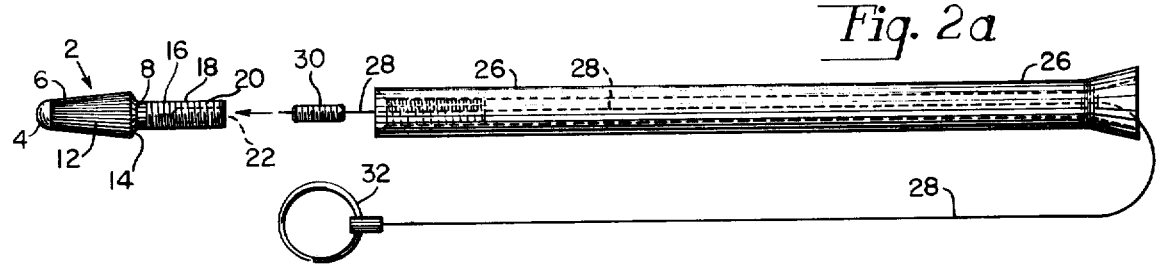
FIGS. 2a–2c illustrate the assembly of the device prior to use.
Figure 2B:
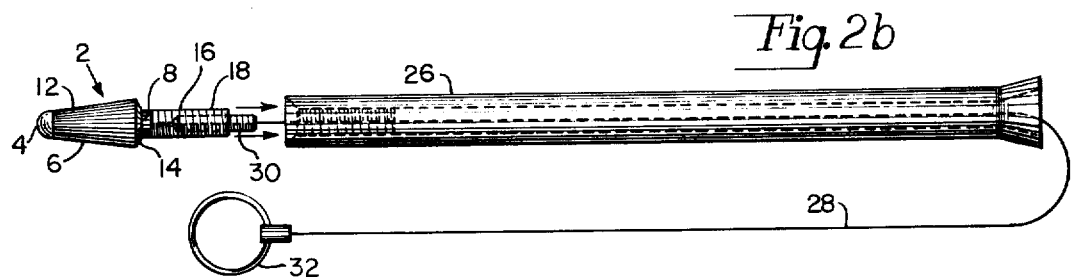
Figure 2C:
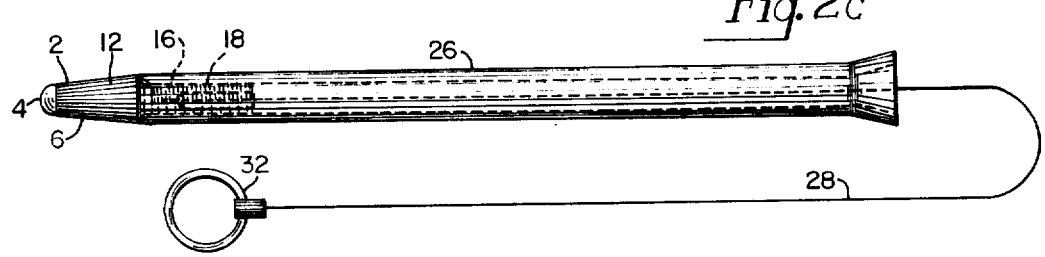

Prior to use, the safety wire 28 is passed through the catheter 26 (FIG. 2a) and connected to the member 2 (FIG. 2b) which is in turn screwed into the catheter 26 (FIG. 2c). The assembly is then in condition for use.

The device is particularly useful in the case of occlusion of arteries wherein an artery is blocked, or nearly so, by accumulation of atherosclerotic plaque on the inside wall of the artery, occluding or greatly reducing the flow of blood therethrough. To effect repair of such an artery, the artery A is incised at the site of the occlusion (FIG. 3b) and plaque P is removed (FIG. 3c). The device 2, with catheter 26 attached, is introduced in the incision, member 2 going first, and fed along the incised artery A until the member 2 reaches and enters the intact distal portion Ad of the artery (FIG. 3d).

Upon twisting of the catheter 26, the member 2 is caused to rotate, thereby causing the ridges or knurls 12 to ream the interior of the distal artery, whereby to remove distal plaque accumulated therein (FIG. 3d). The conical configuration of the body portion 6 of the device operates to taper the distal plaque. A patching operation in which the incised portions of the artery are sewn to a patch member R, is then undertaken, the member 2 being used as a form for supporting the flexible walls of the artery A and the patch R and deflecting and guiding the incoming surgical needle point (FIG. 3e).

Upon completion of the reaming and sewing operation, the device is withdrawn through the remainder of the incision in the artery (FIG. 3f) which must then be closed in accordance with known procedures (FIG. 3g).

In the event the catheter 26 and the device 1 become separated, the safety wire 28 may be used to extract the device from the artery, the chamfered surface 14 (FIG. 1) facilitating the safe backward movement of the member 2 in the artery.

Preferably, the device of the present invention is constructed of molded rigid plastic, such that the item may be packaged in a sanitary manner and discarded after use. The safety wire may be of metal or of a strong plastic material, such as nylon or other suitable material. The catheter per se is known in the art and is usually of a soft flexible plastic. The device may alternatively be made of stainless steel or other suitable metal, though requiring sterilization between uses.

It is to be understood that the present invention is by no means limited to the particular embodiments herein disclosed and/or shown in the drawings, but also comprises any modifications or equivalents within the scope of the disclosure. For example, the illustrative procedure described herein comprises the endarterectomic use of the device. It will be apparent to those skilled in the art, that the present device and method find equal facility in the performance of anastomotic-type procedures, wherein two incisions are made, at either end of an affected area, and a by-pass end sewn to each incision. In such case, the device is first fed through the by-pass and into the distal incision and subsequently withdrawn from the by-pass, if desired, all in accordance with the invention herein described.

Having thus described my invention, what I claim as new and desire to secure by Letters Patent of the United States is:

1. A device for surgical use in repairing arteries, said device comprising a substantially rigid member having a smooth rounded first end and a generally conically shaped body portion extending therefrom toward a second end, said substantially rigid member having on said body portion thereof a plurality of ridges extending from said smooth first end to said second end and adapted to engage interior walls of an artery and plaque disposed thereon, said device, upon insertion into an incised artery being adapted to center itself within said artery, to support said artery and guide and deflect a surgical needle penetrating the wall of said artery and, upon turning of said device to ream the interior wall of said artery and to taper said plaque.

2. The invention according to claim 1 in which said device further comprises connector means extending from said rigid member.

3. The invention according to claim 2 in which said connector means comprises a shank extending from said second end of said rigid member.

4. The invention according to claim 3 in which said shank has first means for connection thereof to a catheter and second means for connection thereof to a safety wire.

5. The invention according to claim 1 in which said device is provided with a flow passage to facilitate the passage of fluid therethrough.

6. The invention according to claim 1 in which said second end is provided with a beveled circular edge to facilitate rearward movement of said device in said artery.

7. The invention according to claim 3 in which said shank comprises external threads for engaging the internal walls of a catheter.

8. The invention according to claim 7 in which said second end is provided with a beveled outer edge and one end of said catheter abuts said bevel.

9. The invention according to claim 6 in which one end of said flow passage is in communication with a catheter connected to said device.

* * * * *